US00PP23514P2

(12) United States Plant Patent
Kordes

(10) Patent No.: US PP23,514 P2
(45) Date of Patent: Apr. 9, 2013

(54) SHRUB ROSE PLANT NAMED 'KORELFKOLO'

(50) Latin Name: *Rosa hybrida*
Varietal Denomination: KORelfkolo

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 13/135,806

(22) Filed: Jul. 14, 2011

(51) Int. Cl.
*A01H 5/00* (2006.01)

(52) U.S. Cl. ..... Plt./108

(58) Field of Classification Search ..... Plt./108
See application file for complete search history.

*Primary Examiner* — Kent L Bell

(57) ABSTRACT

A new and distinct variety of rose with long lasting, novel salmon-red flowers, and attractive foliage with excellent disease resistance. It exhibits an upright to bushy habit with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORelfkolo'.

CROSS REFERENCES AND FEDERAL R&D STATEMENT

There are no cross referenced or related applications. This variety was developed without the aid of any research grant.

The new variety of rose plant of the present invention originated from a controlled crossing in a breeding program of two distinct parents during the summer of 2001. The crossing was between an 'un-named seedling' and an 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORelfkolo'.

SUMMARY OF THE INVENTION

The new rose plant may be distinguished from its seed parent, an 'un-named seedling', by the following combination of characteristics:

1. The seed parent has dark red blooms while 'KORelfkolo' has bright salmon-red blooms.
2. 'KORelfkolo' has flower blooms that are 80-90 mm in diameter while the seed parent's blooms are 50-70 mm in diameter.

The new rose plant may be distinguished from its pollen parent, an 'un-named seedling' by the following combination of characteristics:

1. The pollen parent has dark red blooms while 'KORelfkolo' has salmon-red blooms.
2. 'KORelfkolo' has glossy leaves while the pollen parent has semi matte leaves.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORelfkolo' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORelfkolo' was selected in May, 2002 from the seedling beds to be asexually propagated for further evaluation. The first asexual propagation of 'KORelfkolo' was done by budding to seedling understocks in July, 2002 at the inventor's nursery in Offenseth-Sparrieshoop, Germany.

This initial and other subsequent propagations conducted in controlled environments demonstrate that 'KORelfkolo' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORelfkolo'.

DETAILED BOTANICAL DESCRIPTION

The following is a description of 'KORelfkolo', as observed growing in June, 2011 in a nursery in Jackson County, Oreg. on plants of 1 year of age. Color references are made using The Royal Horticultural Society (London, England) Colour Chart, 2001 except where common terms of color are used.

For a comparison, several physical characteristics of the rose variety 'KORcasima', a rose variety from the same inventor described and illustrated in U.S. Plant Pat. No. 20,732 and issued on Feb. 9, 2010 are compared to 'KORelfkolo' in Chart 1.

CHART 1

| Characteristic | 'KORelfkolo' | 'KORcasima' |
|---|---|---|
| Petal count: | Approximately 12-15 petals. | Approximately 70-80 petals. |
| Flower color, general tonality: | Red Group 52A. | Red Group 53A. |
| Foliage texture: | Upper: Semi-glossy and glabrous. | Upper: Semi glossy and smooth. |

Parents:

*Seed parent*.—An 'un-named seedling'.

*Pollen parent*.—An 'un-named seedling'.

Classification:

*Botanical classification*.—*Rosa hybrida* 'KORelfkolo'.

*Commercial classification*.—Shrub rose.

FLOWER AND FLOWER BUD

Blooming habit: Continuous.

Flower bud:

*Size*.—Upon opening, 30 mm in length from base of receptacle to end of bud and 25 mm diameter at its widest point.

*Bud form*.—Long. Pointed ovoid.

*Bud color*.—As sepals first unfold, bud color is Red Group 47A. When ¼ open, the upper surface of petals is Red Group 46B, and the lower surface is Red Group 46C. Guard Petals are Red Group 46B.

*Sepals*.—Color: Upper surface: Green Group 138A. Lower surface: Yellow-Green Group 146B. Size: Average 25-35 mm (l)×8-10 mm (w). Base: Flat at union with peduncle. Shape: Strong. Strong foliaceous appendages on three of the five sepals. Apex: Foliaceous appendages on 3 sepals. The distal ends of two of the sepals are apiculate. Surface texture: Upper side: Strongly pubescent. Lower surface: slight pubescence with limited stipitate glands. Margins: Generally smooth with a few stipitate glands.

Receptacle:

*Surface*.—Generally smooth.

*Color*.—Between Yellow-Green Group 146B and Yellow-Green Group 164C, with intonations of Greyed-Purple Group 184C.

*Shape*.—Urn-shaped.

*Size*.—10 mm (h)×8 mm (w).

Peduncle:

*Surface*.—Smooth.

*Length*.—30 to 40 mm average length.

*Diameter*.—4 to 6 mm average diameter.

*Color*.—Yellow-Green Group 146C.

*Strength*.—Strong.

*Borne*.—Multiple flower buds per stem, generally 1 to 8.

*Anthocyanin*.—Greyed-Purple Group 184A.

Flower bloom:

*Fragrance*.—Moderate.

*Duration*.—On the plant 3-4 days. As a cut flower, 2 to 3 days. Senesced petals drop away cleanly.

*Size*.—Medium. When open, the average flower diameter is 80 to 90 mm and the average flower height is 30-35 mm.

*Form*.—Shape of flower when viewed from the side: Upon opening, upper part: Flattened convex. Upon opening, lower part: Concave. Open flower, upper part: Convex. Open flower, lower part: Concave.

Color:

*Upon opening, petals*.—Outermost petals: Outer Side: Red Group 50A. Inner Side: Red Group 50A. Innermost petals: Outer Side: Red Group 50A. Inner Side: Red Group 50A.

*Upon opening, basal petal spots*.—Basal petal spot, outermost petals: Outer Side: Yellow Group 3B. Inner Side: Yellow Group 3D. Basal petal spot, innermost petals: Outer Side: Yellow Group 3C. Inner Side: Yellow Group 3B.

*After opening, petals*.—Outermost petals: Outer Side: Red Group 53C. Inner Side: Red-Purple Group N57A. Innermost petals: Outer Side: Red Group 57A. Inner Side: Red-Purple Group N57A.

*After opening, basal petal spots*.—Basal petal spot, outermost petals: Outer Side: White Group 155A. Inner Side: White Group 155B. Basal petal spot, innermost petals: Outer Side: White Group 155C. Inner Side: White Group 155C.

General tonality: On open flower Red Group 52A. No change in the general tonality at the end of the 2nd day. Afterwards, general tonality is Red Group 153C.

Petals:

*Petal count*.—Semi-Double. Approximately 12-15 petals under normal conditions, with 0-3 petaloids.

*Petal reflex*.—Petals reflex slightly.

*Petal edge*.—Retuse.

*Petal shape*.—Obtuse. Apex shape is round. Shape of base is deltoid.

*Petal size*.—About 45-50 mm long and about 35-40 mm wide.

*Thickness*.—Average.

*Petal arrangement*.—Not formal.

Petaloids: Usually a few present.

*Petaloid count*.—Average of 5-8 per flower.

*Average size*.—Length 5 mm. Width 1-2 mm.

*Petaloid color*.—Color of inner side is Red Group 51B. Color of outer side is Red Group 51C.

*Petaloid texture*.—Smooth.

*Margins*.—Indented.

*Petaloid shape*.—Overall shape is deltoid. Apex: Deltoid. Base: Attenuate.

Reproductive organs:

*Pistils*.—Approximately 15-20 present. Stigmas: Location: Slightly inferior in position to anthers. Color: Greyed-Yellow Group 161C. Styles: Length: 8 mm long on average. Color: Yellow-Green Group 146D. With intonations of Greyed-Red Group 182D.

*Stamens*.—Approximately 30-40 on average and regularly arranged. Anthers: Size: 7 mm long. Pollen: Present. Color: Greyed-Yellow Group 163D with intonations of Greyed-Red Group 181C. Filaments: Color: Green-Yellow Group 1B. Length: 8-9 mm on average.

THE PLANT

*Growth*.—Vigorous.

*Plant habit*.—Upright to bushy habit. When grown as a budded field plant, the average height of the plant itself is 80 cm and the average width is 70 cm.

*Blooming*.—Floriferous.

*Stems*.—Stem color: Young wood: Yellow-Green Group 146B. Older wood: Yellow-Green Group 146C. Stem surface: Young wood: Smooth. Older wood: Smooth.

*Prickles*.—Present. Incidence: 7-10 per 10 cm of stem. Size: Average length: 4-6 mm. Color: Immature prickles: Greyed-Purple Group 185B. Mature prickles: Greyed-Red Group 182C. Shape: Concave. Anthocyanin: None observed.

*Leaves and leaflets*.—Leaflet just below bud clusters are thin, 30 mm long and 2-3 mm wide, not forming a full leaflet. Normally 5 leaflets on normal leaves in middle of the stem. Venation pattern: Pyramidal net pattern. Leaf size: 120 mm (l)×10 mm (w). Abundance: Average. Texture: Upper side of leaflet: Semi-glossy and glabrous. Under side of leaflet: Matte and glabrous. Leathery. Color, mature foliage: Upper Leaf Surface: Yellow-Green Group 147A. Lower Leaf Surface: Yellow-Green Group 146B. Color, juvenile foliage: Upper Leaf Surface: Green Group 137A. Lower Leaf Surface: Yellow-Green Group 147B. Anthocyanin intonation: Present. Intonations present on juvenile foliage of Greyed-Purple Group 183B.

*Stipules*.—Average size: 20 mm (l)×4 mm (w). 1 stipule per compound leaf. Stipule color: Yellow-Green Group 147C. Anthocyanin: Greyed-Purple Group 184C. Stipitate glands: Limited numbers present on margins. Shape: Apex: Apiculate. Base: Winged.

*Petiole*.—Length: 25 mm. Diameter: 2-3 mm. Petiole color: Yellow-Green Group 147C. Margins: Prickles with stipitate glands. Anthocyanin: Greyed-Purple Group 183B on juvenile foliage. Prickles: On undersides and along margins. Stipitate Glands: Present.

*Petiole rachis*.—Length: 20 mm on average. Diameter: 1-2 mm on average. Color: Yellow-Green Group 147C. Underneath: On mature foliage, with prickles and occasional thorns. Margins: Prickles and stipitate glands. Stipitate glands: Limited numbers of stipitate glands on margins.

*Leaflets*.—Size: Average size of the terminal leaflet is 55-60 mm (l)×35 mm (w). Shape: Entire leaflet: Ovate. Base: Obtuse. Apex: Acute. Margins: Finely serrated. Surface: Upper: Moderately glossy. Lower: Matte. Texture: Glabrous and semi-glossy. Arrangement: Pinnate Venation: Reticulate.

Hips/seed formation: None observed.

Winter hardiness: To date, the variety has been grown successfully in Zone 5.

Disease resistance: Excellent resistance to Powdery mildew (*Sphaerotheca pannosa*), rust (*Phragmidium disciflorum*), and blackspot (*Diplocarpon rosae*). diseases under normal growing conditions.

I claim:

1. A new and distinct variety of rose plant, as described and illustrated herein.

* * * * *

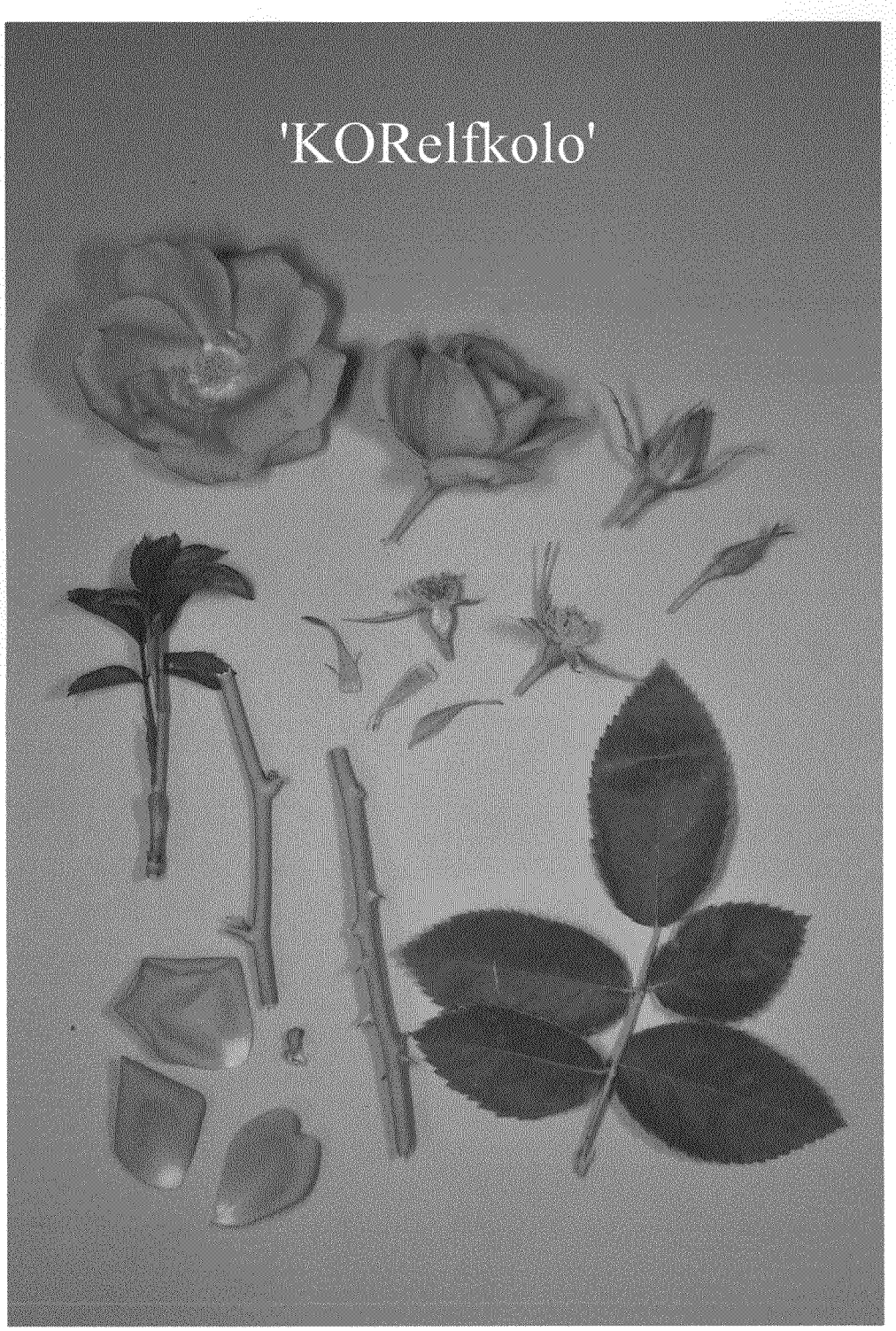
'KORelfkolo'